United States Patent
Hunter et al.

[11] Patent Number: 6,159,459
[45] Date of Patent: Dec. 12, 2000

[54] ORAL LUBRICATING COMPOSITION

[75] Inventors: Catherine M. Hunter, Highland Park; Abdul Gaffar, Princeton; Theresa D. Mordarski, East Brunswick, all of N.J.

[73] Assignee: Colgate Palmolive Company, New York, N.Y.

[21] Appl. No.: 08/432,484

[22] Filed: May 1, 1995

[51] Int. Cl.[7] .............................. A61K 6/00; A61K 7/16
[52] U.S. Cl. ...................... 424/78.08; 424/49; 424/48; 424/440; 514/772.1
[58] Field of Search ................... 424/78.08, 435; 514/772.1

[56] References Cited

U.S. PATENT DOCUMENTS

| | | | |
|---|---|---|---|
| 4,088,788 | 5/1978 | Ream et al. | 426/3 |
| 4,438,100 | 3/1984 | Balsleu | 424/609 |
| 4,774,093 | 9/1988 | Provonchee et al. | 424/493 |
| 4,820,506 | 4/1989 | Kleinberg et al. | 424/40 |
| 4,900,722 | 2/1990 | Williams et al. | 514/54 |

FOREIGN PATENT DOCUMENTS

| | | | |
|---|---|---|---|
| 0613684 | 9/1994 | European Pat. Off. | A61K 9/00 |
| 9520971 | 8/1995 | WIPO | A61K 33/42 |

OTHER PUBLICATIONS

J.E.F. Reynolds: Martindale, the Extra Pharmacopoeia, 30th edition, 1993, p. 1218.

Patent Abstracts of Japan vol. 010, No. 350 (C–387), Nov. 26, 1986 & JP,A,61 151118 (Daicel Chem. Ind. Ltd.), Jul. 9, 1986.

Biorrheology, vol. 31, No. 6, 1994 p. 631–642, XP000577817, W.A. Van Der Reijden: "Rheological Properties of Commercially available Polysaccharides with Potential Use in Saliva Substitutes".

Derwent Publications Ltd., London, GB: AN 91–084479 [12] XP002014167 & JP,A, 03, 031 210 (Kao Corp.), Feb. 12 1991.

*Primary Examiner*—Thurman K. Page
*Assistant Examiner*—P. Kulkosky
*Attorney, Agent, or Firm*—Paul Shapiro

[57] ABSTRACT

An oral lubricant having particular usefulness for alleviating the symptoms of xerostomia based on a beta-glucan polymer in an orally acceptable carrier or vehicle.

18 Claims, 6 Drawing Sheets

ORAL LUBRICATING COMPOSITION

BACKGROUND OF THE INVENTION

1. Field of the Invention

The invention relates generally to an oral composition having a lubricating function. More particularly, the invention relates to a composition for relieving the soft-tissue disorders associated with xerostomia, the active ingredient of the composition being a beta-glucan polymer.

The invention also encompasses a method of treating xerostomia comprising administering to an affected individual a lubricant composition containing a beta-glucan polymer in an orally acceptable vehicle.

2. The Prior Art

Xerostomia commonly known as "dry mouth" is a condition in which the salivary glands do not produce sufficient quantities of saliva. This causes discomfort which can in some cases be quite severe. Without saliva, the mouth burns and the throat and tongue can undergo radical changes. Teeth can decay rapidly and the tongue can become smooth, cracked and vulnerable to infection.

The mouth is one of the body areas most exposed to the external environment. Normally, mucous forms a continuous protective layer in the nose, mouth and throat. A patient suffering from xerostomia not only has decreased fluid in the mouth, but also an insufficient quantity of mucoproteins and mucopolysaccharides to hold fluid in contact with the cells and create a barrier to irritation and infection.

Cases of xerostomia may vary from the mild, in which only slight dryness is experienced, to severe cases in which the patient will have serious problems with mastication, swallowing, digestion, speech, and the like. As noted in U.S. Pat. No. 4,438,100 to Balslev et al., there are a number of causes of xerostomia, including the physiological (e.g., age, menopause, postoperative conditions, dehydration), as well as the psychic (nervousness). The reasons for mouth dryness may also be pharmacological (e.g., as a common side effect of many medications, including anti hypertensives, diuretics, anti-arthritics and anti-depressants) or as a result of radiotherapy. The most severe cases of xerostomia are caused by radiation therapy after head and neck surgery and by autoimmune diseases such as lupus, Sjögrens Syndrome, and rheumatoid arthritis.

Until recently, the treatments for xerostomia have had significant drawbacks. For example, symptoms of mild xerostomia can be somewhat alleviated by consumption of fluids, hard candy and throat lozenges. Because of the susceptibility of xerostomia patients to tooth decay and gum disease, however, the increased sugar intake associated with conventional candy and lozenges is of real concern. In addition, fluids or candy are typically not effective with more severe cases of xerostomia, nor do they provide long-lasting relief with mild cases.

Artificial saliva and salivary substitutes have been proposed as palliative treatments for the symptoms of xerostomia, which preparations have physical and chemical properties that simulate those of natural (human) saliva.

Artificial salvias of the prior art include compositions which contain ions that mimic those found in natural saliva; glycerin, as well as carboxymethylcellulose-based preparations to provide the proper level of viscosity. Fluoride ions are sometimes included to prevent demineralization of tooth enamel. These compositions have not found wide acceptance as many patients find, that such preparations are irritating or distasteful, and that their lubricating effect is of relatively short duration. This lack of wide acceptance is believed due, at least in part to the fact that the artificial saliva preparations of the prior art do not fully possess the rheological characteristics of natural saliva which are responsible for natural saliva's lubricating effect. An article entitled "Lubrication and Viscosity Features of Human Saliva and Commercially Available Saliva Substitutes", M. N. Hatton et al, J. Oral Maxillotac. Surg. 45, 496–499 (1987), contains a full discussion of the problems associated with the presently available commercial saliva substitutes in the treatment of individuals with diminished salivary gland function.

In view of the problems which occur when salivary secretion is deficient, it will be understood that it would be most desirable to have an oral lubricating composition for human use, to relieve the above-mentioned discomforts and inconveniences incurred by xerostomia or by a greater or lesser tendency to dryness of the mouth. Such a composition should have rheological properties which are as close to the properties of the natural salivary secretion as possible and exhibit improved lubricity so as to provide to the patient long term relief from the symptoms of xerostomia or dry mouth.

SUMMARY OF THE INVENTION

It has been determined by the inventors that rheologically, saliva is a pseudo-plastic, low viscosity material, that undergoes shear thinning at low torque, is viscoelastic with a dominant elastic component and recovers quickly after the application of a shear force.

The present invention is premised on the surprising discovery that a beta-glucan polymer is extremely effective in simulating the rheological characteristics of natural saliva and can be incorporated at low concentrations into compositions that are lubricious and provide long-lasting relief in cases of mild to severe xerostomia, with no unpleasant side effects.

Thus the present invention provides a method for treating xerostomia comprising orally administering, to an affected individual, a beta-glucan polymer containing composition in an amount effective to alleviate the symptoms of dry mouth. The beta-glucan polymer may be administered in an orally acceptable vehicle in liquid, paste, gum or lozenge form. In addition to the beta-glucan polymer, one or more sweeteners which are preferably noncariogenic, flavors, and a salivary stimulant such as citric acid may also be used in combination with the beta-glucan polymer.

DETAILED DESCRIPTION OF THE PREFERRED EMBODIMENTS

Figure 1A:
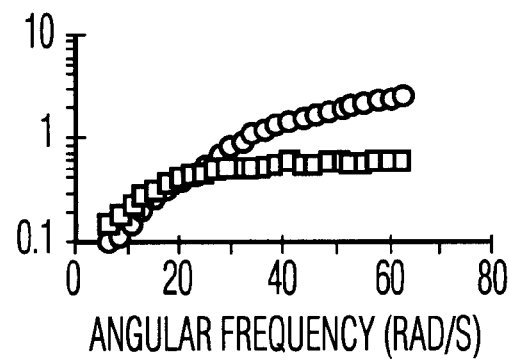
FIG. 1 shows the elastic structure of beta-glucan polymer (Scleroglucan) aqueous solutions of varying concentration compared with natural saliva as a function of the relation between G' (storage modulus) and G" (loss modulus) at varying angular frequencies (6.3 to 63 radians/sec.) and an applied torque (10 $\mu$Nm).
Figure 1B:
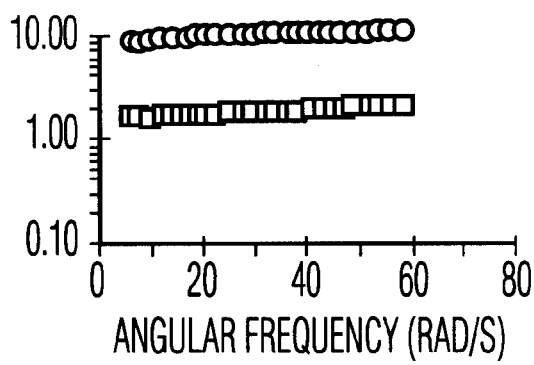
Figure 1C:
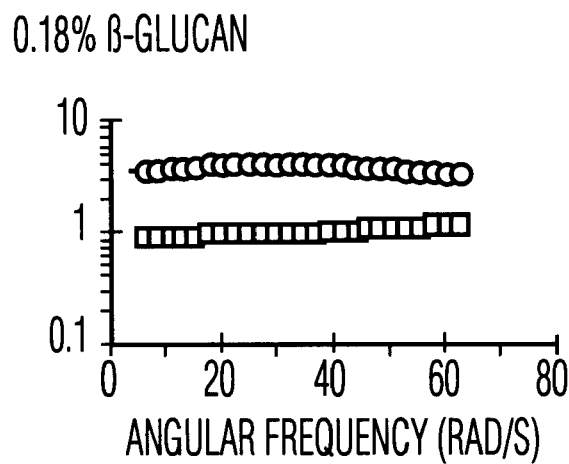
Figure 1D:
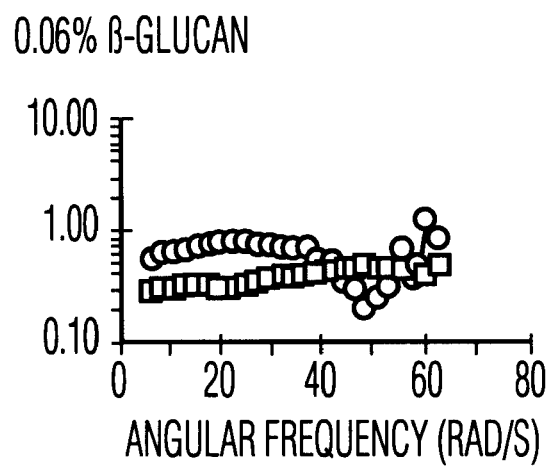
Figure 2A:
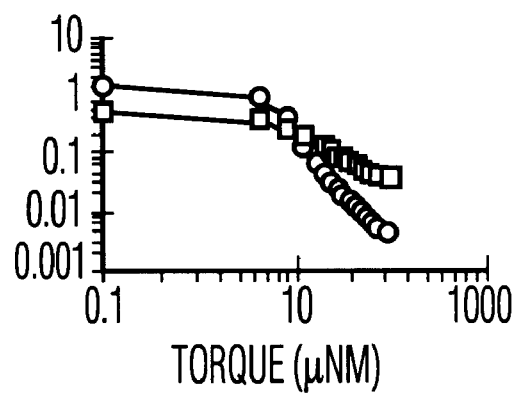
FIG. 2 shows the shear thinning behavior of beta-glucan polymer (Scieroglucan) aqueous solutions of varying concentrations compared with natural saliva, shear thinning being a function of the relation of the angular frequency at 6.3 radians/sec. and a varied applied torque (0.1 to 100 $\mu$Nm).
Figure 2B:
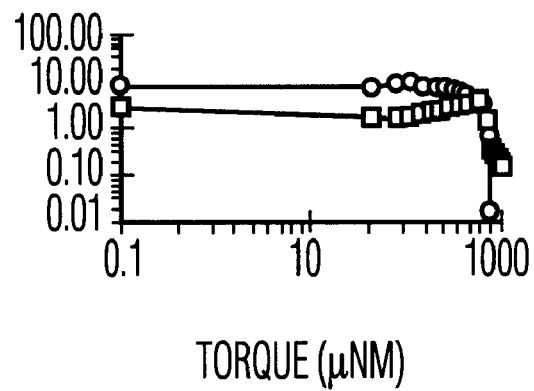
Figure 2C:
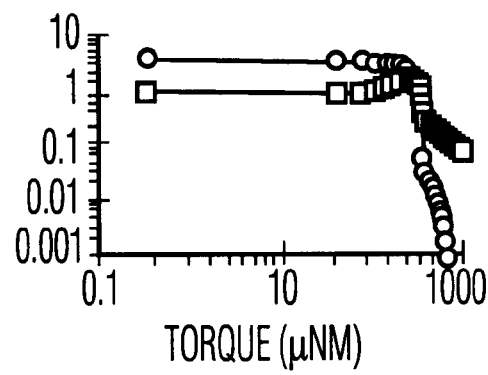
Figure 2D:
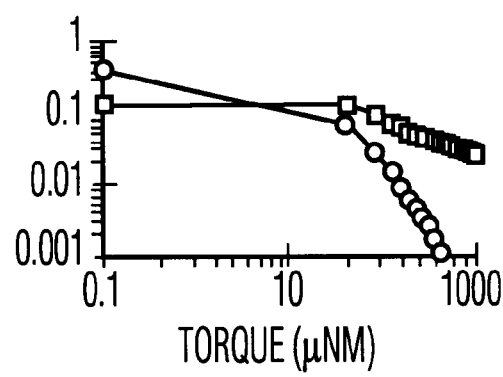

Beta-glucan polymers are known to the art and are polymers of glucose derived from yeast, bacteria, fungi and plants. Glucan polymers containing a beta (1-3) linked glycopyranose backbone are used in accordance with the practice of the present invention to prepare liquid compositions which simulate the rheological properties of natural saliva. Particularly useful are glucan polymers comprised of a backbone chain of beta (1-3) linked glucose units with a low degree of intramolecular branching through beta (1-6) linkages.

A preferred beta-glucan polymer is Scleroglucan, a non-ionic water soluble polymer, isolated from sclerotium glucanicum, the polymer having a triple-helical beta-1,3-linked glucopyranose backbone with a single beta-1,6-linked glucopyranosyl branch every third subunit. The triple helix structure differentiates Scleroglucan from carbohydrate gums such as the xanthans.

Scleroglucan has the structural formula

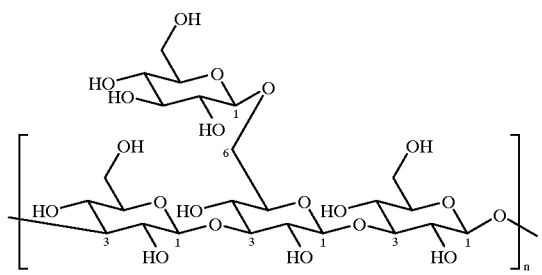

wherein n indicates multiple repeating monomer units.

In addition to Scieroglucan, other beta-glucan polymers derived from yeast, bacteria and fungi such as poly (1,6)-B-D-glucopyranosyl-(1-3) glycopyranose may be used in the practice of the present invention.

The manufacture of Scleroglucan and its derivatives are disclosed in U.S. Pat. No. 3,301,848, the disclosure of which is incorporated herein by reference in its entirety. Scleroglucan is disclosed in U.S. Pat. No. 3,372,749 and U.S. Pat. No. 4,347,146 for use as a thickening agent for an aqueous drilling fluid in processes for producing petroleum from petroleum-bearing subterranean formations. U.S. Pat. No. 4,647,312 discloses polyvalent metal ion complexes of Scleroglucan as thickeners for aqueous fluids used in oil production processes.

In accordance with the present invention compositions containing beta-glucan polymers for oral application may be in any convenient form, such as a mouthrinse, spray, tablet, lozenge, chewing gum, or toothpaste.

A mouthrinse or throat spray may be prepared by mixing the beta-glucan polymer with an aqueous vehicle containing flavoring oil, nonionic surfactant, humectant, sweetener and preservative.

A typical mouthrinse or spray prepared in accordance with the practice of the present invention contains the following ingredients in percent by weight based on the weight of the total formulation.

| Ingredient | % by Weight |
| --- | --- |
| Beta-glucan polymer | 0.005–5.0 |
| Flavor | 0.5–2.0 |
| Surfactant | 0.25–3.0 |
| Humectant | 10–30 |
| Sweetener | 3–10 |
| Preservative | 0.1–1.0 |
| Water | 65–80 |

Examples of flavors useful in the practice of the present invention include essential oils such as peppermint oil, spearmint oil and methylsalicylate (oil of wintergreen) and citrus/fruit flavors.

Surfactants useful in the practice of the present invention include non-ionic organic surface active polymers such as polyoxyethylene-polyoxypropylene block copolymers such as Pluronic 108 and Pluronic F-127 marketed by BASF. Pluronic 108 has a molecular weight of 3200 and contains 80% of the hydrophilic polyoxyethylene moiety and Pluronic F127 has a molecular weight of 4000 and contains 70% polyoxyethylene. The surfactant assists in achieving thorough and complete dispersion of ingredients throughout the oral cavity and renders the compositions more cosmetically acceptable. Non-ionic surfactants also maintain the flavoring materials in solution (i.e., solubilizes flavor oil). In addition, non-ionic surfactants are compatible with the beta-glucan polymers of its invention, providing for a stable, homogeneous composition.

Humectants used to prepare the aqueous vehicle include glycerin, sorbitol and polyethylene glycol of molecular weight 400–2000.

Examples of preservatives useful in the practice of the present invention include benzoic acid, sodium benzoate and cetylpyridinium chloride. Sweeteners include xylitol, saccharin and sorbitol.

When used for the treatment of xerostomia, a salivary stimulant compound such as citric acid, ascorbic acid or xylitol is included in the oral composition of the present invention at a concentration of about 0.25 to 3% by weight. In addition, a calcium salt such as calcium phosphate or monobasic calcium phosphate is included in the composition at a concentration of about 0.02 to about 5% by weight for the purpose of providing a calcium reservoir to protect tooth enamel from demineralization.

A typical dentifrice such as a toothpaste or gel prepared in accordance with the practice of the present invention contains the following ingredients in percent by weight based on the weight of the total dentifrice.

| Ingredient | % by Weight |
| --- | --- |
| β-glucan polymer | 0.01–5.0 |
| Polishing agent | 3–20 |
| Surfactant | 0.4–2 |
| Humectant | 20–60 |
| Thickener | 0.5–15 |
| Fluoride salt | 0.1–1 |
| Sweetener | 0.1–.7 |
| Flavor | 0.1–1 |
| Water | 15–30 |
| Colorant | 0–1 |

Polishing agents useful to prepare the dentifrice compositions of the present invention include finely divided silica, dicalcium phosphate, calcium pyrophosphate, sodium bicarbonate, insoluble sodium metaphosphate and tricalcium phosphate.

Surfactants include alkali metal alkyl sulfates of 8 to 20 carbon atoms, preferably of 10 to 18 and more preferably of 12 to 16 carbon atoms in the alkyls thereof such as sodium lauryl sulfate and sodium lauryl phosphate. Other useful surfactants include sodium cocomonoglyceride sulfate, sodium linear tridecylbenzene sulfonate, N-lauroyl and N-methyl taurate.

Thickeners include silica thickeners, carob bean gum, carrageenan gum, hydroxymethyl cellulose, hydroxypropyl cellulose and alginates.

Humectants include glycerol, sorbitol, propylene glycol, polypropylene glycol and/or mannitol.

Aspartame or saccharin may be used as the artificial sweetener, and the flavor may be based principally or partially on limonene and may contain menthol or other physiologically cooling agent to give it a special appeal.

An effective amount of the beta-glucan polymer, e.g., about 0.01–5% may be incorporated in an inert carrier in the formulation of tablets and lozenges. A typical lozenge formula contains the following ingredients, in percent by weight, based on the weight of the total formulation:

|  | % by Weight |
|---|---|
| Beta-glucan polymer | 0.01–5 |
| Humectant | 75–98 |
| Emulsifier | 1–20 |
| Tableting Lubricant | 0.1–5 |
| Sweetener | 0.2–2 |

Suitable humectants include sorbitol and glycerin. Emulsifiers include nonionic polyoxyesters such as polyoxyethylene sorbitan fatty esters e.g. polyoxyethylene 20 sorbitan monolaurate commercially available under the tradenames Polysorbate 20 and Tween 20, tableting lubricants include magnesium stearate.

A typical chewing gum may contain the following ingredients in the gum formulation:

| Ingredients | % by Weight |
|---|---|
| Beta-glucan polymer | 0.01–5.0 |
| Gum base (chicle) | 10–50 |
| Binder (starch) | 3–10 |
| Filler (talc) | 5–80 |
| Humectant | 10–30 |
| Flavor | 0.1–5 |

Manufacturing of mouthrinses, sprays and dentifrices of the present invention is comparatively simple because, in general, there is little or no criticality in the order of addition of the various ingredients present in such compositions. In the preparation of a mouthrinse or spray the ingredients are dissolved in water and/or alcohol. In the preparation of dentifrices such as toothpastes and gels, initially one forms a premix in water in which the water soluble ingredients are first dissolved followed by the water insoluble ingredients, if any. If desired, the lipophilic components may be pre-mixed together and such premix can be mixed with the hydrophiles premix, after which the water insoluble particulate materials may then be blended.

Making the chewing gums and lozenges may be by procedures normally employed in manufacturing such products, with the beta-glucan polymer usually preferably being added near the end of the manufacturing process if heat was employed (so as to minimize subjection to elevated temperatures).

All the processes for manufacturing the described compositions may be carried out at room temperature, as a rule, except possibly those for making gum and lozenges, and in such cases heating may be rninimized to the extent that such is practicable.

The following examples serve to provide further appreciation of the invention but are not meant in any way to restrict the effective scope of the invention. All percentages throughout the specification and claims are by weight % of the final composition unless otherwise indicated and wherein all percentages will total 100% of ingredients in the final composition.

EXAMPLE I

The lubricity effect of the beta-glucan polymer Scleroglucan on the frictional properties of a mucosal membrane surface was compared to human saliva in an in vitro test using a Dermal Torque Meter manufactured by Dia-Stron Ltd., Broomal, Pa. In this test a dynamically driven probe is applied to a mucosal membrane segment with a fixed normal force. The probe is rotated so that the torque applied to the membrane surface increases in small steps. As each torque is applied, the resulting angular deflection of the probe is measured. A plot of this instantaneous angle of deflection versus the applied torque is used to estimate the force required to overcome the static friction between the probe and the membrane. A biphasic model is fit to the data, and the inflection point where deflection starts to increase rapidly is used to approximate the instant where static friction is overcome and the probe breaks free from the membrane. The coefficient of static friction, $\mu$, is then calculated from the normal force and the torque at this break point, using the following formula:

$$\mu = \frac{\text{torque/probe radius}}{\text{normal force}}$$

In a series of tests using varying amounts (0.06–0.30% by weight) of the beta-glucan polymer Scleroglucan dissolved in water, the lubricity of the polymer solutions was compared to stimulated natural (human) saliva by determining the degree to which each solution reduces $\mu$ from a saline solution (0.85% NaCl in water) baseline. Each solution was tested on a fresh piece of membrane and compared to a saline baseline measured for the same membrane. The values of $\mu$ for saline varied from membrane to membrane, depending on the surface properties of the membranes. The results of these tests are recorded in the Table 1 below.

TABLE 1

Static Frictional Coefficient ($\mu$) Compared to Saline Solution

| Test Solution | $\mu$ test solution | $\mu$ saline | % Reduction |
|---|---|---|---|
| Saliva | 0.465 | 0.807 | 42 |
| 0.06% β-glucan* | 0.517 | 1.208 | 57 |
| 0.18% β-glucan* | 0.382 | 1.159 | 67 |
| 0.30% β-glucan* | 0.345 | 1.168 | 70 |

*Scleroglucan

By reference to Table I it is immediately apparent that each solution containing the beta-glucan polymer reduced static friction to a greater degree (57–70%) than saliva (42%).

EXAMPLE II

To assess the saliva-like mouthfeel properties of the beta-glucan polymer Scleroglucan, the polymer solutions of Example I were examined rheologically, using a Carri-Med CS rheometer available from Carri-Med, Inc., Valley View, Ohio. To exhibit a saliva-like mouth feel it has been determined that the viscoelastic properties of the artificial saliva should include an elastic structure, shear thinning behavior, recovery of structure following break down and viscosity comparable to human saliva, over a range of shear rates.

Elastic Structure

Samples of the Scleroglucan solutions as well as human saliva were subjected to rotations with angular frequencies varying from 6.3 to 63 radians/sec with an applied torque of 10 $\mu$Nm. For each solution tested, the storage modulus (G') and the loss modulus (G") were measured over this angular frequency range and compared. The elastic structure of a viscoelastic substance is reflected by the relative magnitude of G' compared to that of G". This elastic structure is an important characteristic of an oral lubricant as it allows the material to form a protective cushioning interface between opposing hard and soft tissues. As shown in FIG. 1, in each of the Scleroglucan polymer solutions the relative magnitude of G' to G" was comparable to that of natural saliva indicating an elastic character comparable to that of saliva.

Shear Thinning

Shear thinning behavior is important for oral lubrication because, while more structure is required during periods when the mouth is at rest, to provide a protective coating between opposing surfaces the bathing fluid must be able to flow freely under shear conditions such as speaking or swallowing to avoid interfering with such movements.

Shear thinning is characterized by a time dependent decrease in viscosity with increasing shear rate. Likewise, shear thinning results in a decrease in G' with increasing torque. To determine shear thinning characteristics, the Scleroglucan solutions were subjected to rotations with angular frequency of 6.3 radians/sec and an applied torque varying from 0.1 to 100 $\mu$Nm. For each solution tested, G' and G" were followed over this torque range to determine whether G' falls below G" with increasing torque, indicating shear thinning behavior.

As shown in FIG. 2, for the saliva and Scleroglucan solutions tested, G' was greater than G" at low torques and decreased sharply with increasing torque. Saliva demonstrated this shear thinning behavior at torques of approximately 10 $\mu$Nm. The Scleroglucan solutions shear thinned at torques ranging from 70 $\mu$Nm (0.06% $\beta$-glucan) to approximately 500 $\mu$Nm (0.3% $\beta$-glucan) indicating that the Scleroglucan solutions exhibited shearing thinning behavior substantially similar to saliva.

Recovery

Recovery of viscoelastic structure is important for oral lubrication because it allows the bathing fluid to provide both cushioning, under rest conditions, and free-flowing lubrication, during movement such as speaking or swallowing.

Figure 3A:
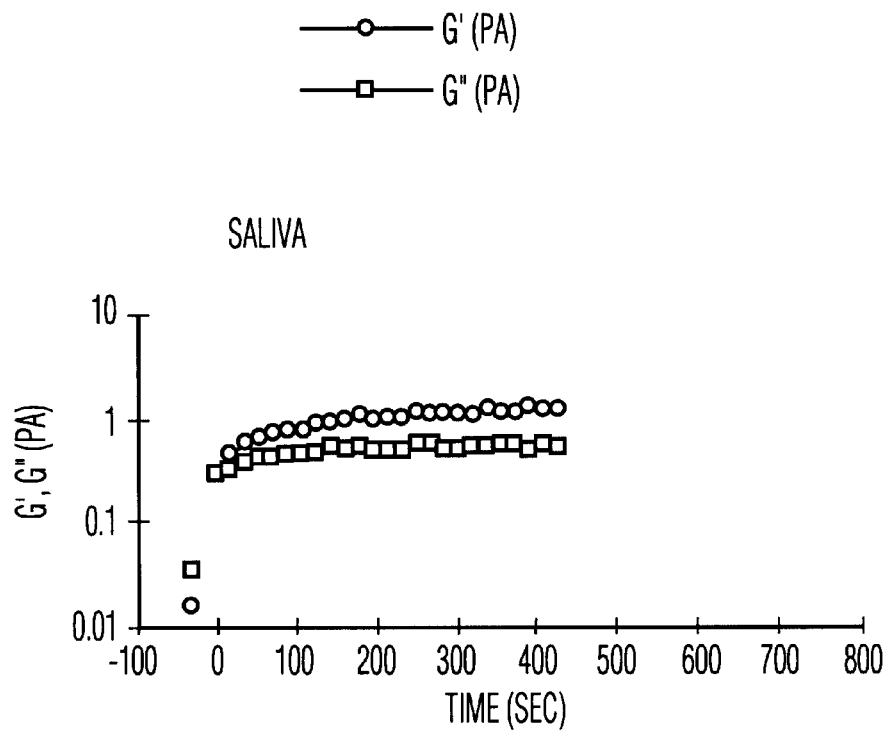
FIG. 3 shows the recovery of viscoelastic structure following shear thinning of a 0.18% beta-glucan polymer (Scleroglucan) aqueous solution compared with natural saliva, recovery being measured as the response over time of G' and G", following a period of steady shear rate (200/sec$^{-1}$).
Figure 3B:
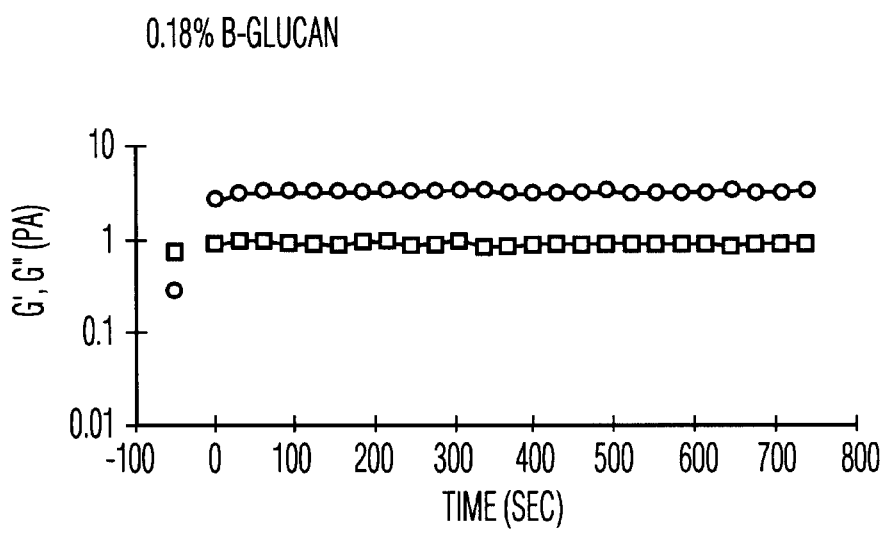

Recovery of viscoelastic structure following shear thinning was determined by measuring the response over time of G' and G", following a period of steady shear rate, that is, 200 sec$^{-1}$ and an angular frequency of 6.3 radians/sec for 30 seconds and then quickly (within 1–3 seconds) reducing the shear rate. G' and G" were then monitored under these low shear rate conditions over time, as shown for saliva and a 0.18% beta-glucan polymer solution containing 0.18% Scleroglucan in FIG. 3. As is apparent from FIG. 3, the first points were recorded 1–3 seconds after the shear rate was reduced by which time some recovery had occurred. The data recorded in FIG. 3 indicate for both saliva and the 0.18% $\beta$-glucan polymer (Scieroglucan) solution, recovery followed the preshear within minutes in both cases.

Viscosity

To provide a natural mouthfeel, the viscosity of the oral lubricant should be similar to that of natural saliva.

Figure 4:
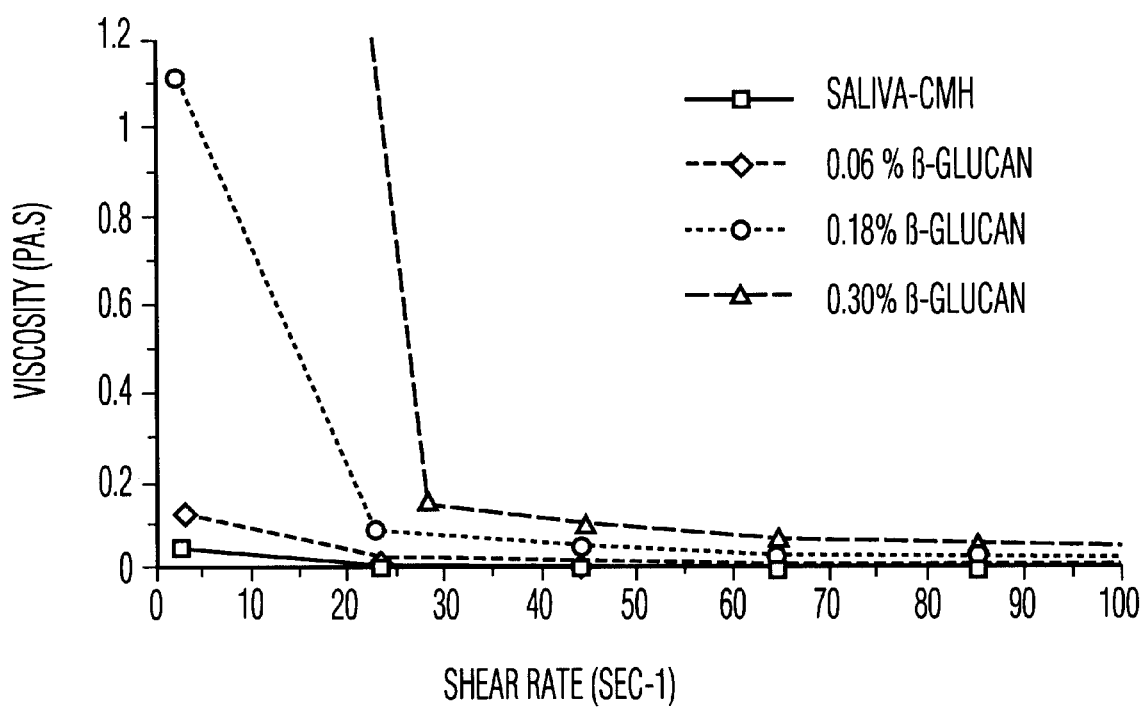
FIG. 4 shows the viscosity of beta-glucan polymer (Scleroglucan) aqueous solutions of varying concentration compared to saliva at varying shear rates.

The viscosities of solutions of the $\beta$-glucan polymer Scleroglucan and of natural saliva were measured as the shear rate was varied from 3 to 600 sec$^{-1}$. The results shown in FIG. 4 indicate that the viscosity, which decreases with increasing shear rate indicating shear thinning behavior, was less for the 0.18% Scleroglucan solution than the 0.3% Scleroglucan solution, but both were more viscous than saliva. The viscosity of the 0.06% solution approached that of saliva.

EXAMPLE III

A mouthrinse composition suitable for use as an oral lubricant has the following composition:

| Ingredient | Weight Percent |
|---|---|
| Scleroglucan | 0.1 |
| Pluronic F108 | 0.5 |
| Pluronic F127 | 0.5 |
| Benzoic acid | 0.02 |
| Sorbitol | 2.0 |
| Flavor | 0.1 |
| Glycerin | 15.0 |
| Xylitol | 6.0 |
| Potassium citrate | 0.75 |
| Citric acid | 0.75 |
| Monobasic calcium phosphate | 0.70 |
| Polydimethylsiloxane emulsion | 0.005 |
| Sodium benzoate | 0.25 |
| Water | 73.325 |
|  | 100.0 |

A mouthrinse of the above formula is made by mixing together the ingredients listed above to make a finished product suitable for use in lubricating the oral cavity.

EXAMPLE IV

A chewing gum suitable for delivery of the $\beta$-glucan polymer lubricant Scleroglucan to the oral cavity has the following composition:

| Ingredient | Weight Percent |
|---|---|
| Scleroglucan | 0.2 |
| Sorbitol/Mannitol mixture (50:50) | 35.25 |
| Flavor, including 0.03% saccharin | 2.0 |
| Chicle base | 20.0 |
| Starch | 10.0 |
| Talc | 32.55 |
|  | 100.0 |

A chewing gum of the above formula is made by mixing together the ingredients listed above to make a finished product that is effective in relieving the symptoms of dry mouth.

EXAMPLE V

A lozenge suitable for delivery of the beta-glucan polymer lubricant Scleroglucan to the oral cavity has the following composition:

| Ingredient | Weight Percent |
| --- | --- |
| Scleroglucan | 0.20 |
| Sorbitol | 98.25 |
| Sodium saccharin | 0.15 |
| Magnesium stearate (tabletting agent) | 0.40 |
| Emulsifer (Polysorbate 20) | 1.00 |
|  | 100.0 |

A lozenge of the above formula is made by melting the sorbitol and dissolving/dispensing the other ingredients in it, after which the mix is allowed to solidify at room temperature. The lozenges so made are effective in relieving the symptoms of dry mouth.

EXAMPLE VI

A toothpaste suitable for delivery of the beta-glucan polymer to the oral cavity has the following composition:

| Ingredient | Weight Percent |
| --- | --- |
| Scleroglucan | 1.0 |
| Sorbitol solution, 70% active, aqueous (22.5 wt. %) | 32.6 |
| Glycerol | 11.0 |
| Carrageenan gum | 0.5 |
| Sodium fluoride | 0.24 |
| Sodium lauryl sulfate | 1.2 |
| Zeodent ® 113 [1] | 17.0 |
| Syloid ® 244 [2] | 3.0 |
| Fumed silica, thickening agent | 0.3 |
| Saccharin | 0.06 |
| Flavor | 1.0 |
| Water | 32.1 |
| TOTAL | 100.0 |

[1] Silica polishing agent, mfd. by J.M. Huber Corp.
[2] Silica thickening agent.

What is claimed is:

1. A method for reducing the discomfort associated with a xerostomia condition in the oral cavity comprising preparing a composition comprised of a beta-glucan polymer in an orally acceptable vehicle in an amount effective to alleviate the discomfort and thereafter periodically applying the composition to the oral cavity to coat the surfaces thereof with the polymer.

2. The method of claim 1 wherein the beta-glucan polymer is Scleroglucan.

3. The method of claim 1 wherein the beta-glucan polymer is present in the vehicle at a concentration of about 0.005 to about 5% by weight.

4. The method of claim 1 wherein the composition is sprayed into the oral cavity.

5. The method of claim 1 wherein the composition is the form of a mouthrinse.

6. The method of claim 1 wherein the composition is administered to the oral cavity in the form of a chewing gum.

7. The method of claim 1 wherein the composition is administered to the oral cavity in the form of a lozenge.

8. The method of claim 1 wherein the composition is administered to the oral cavity in the form of a toothpaste.

9. The method of claim 1 wherein the composition contains a salivary stimulant.

10. The method of claim 9 wherein the salivary stimulant is citric acid.

11. An oral composition comprising a beta-glucan polymer contained in an orally acceptable vehicle in an amount effective to alleviate the symptoms of dry mouth when applied to the oral cavity.

12. The composition of claim 11 wherein the beta-glucan polymer is Scleroglucan.

13. The composition of claim 11 wherein the beta-glucan polymer is present in the vehicle at a concentration of about 0.005 to about 5% by weight.

14. The composition of claim 9 wherein the vehicle is water.

15. The composition of claim 11 wherein a salivary stimulant is included in the composition.

16. The composition of claim 15 wherein the salivary stimulant is citric acid.

17. A chewing gum for treating xerostomia and alleviating the symptoms thereof comprising a beta-glucan polymer and a gum carrier.

18. A lozenge for alleviating the symptoms of xerostomia comprising a shaped solid of a beta-glucan polymer, sweetener and a salivary stimulant acid.

* * * * *